United States Patent [19]

Becker et al.

[11] Patent Number: 4,844,729

[45] Date of Patent: Jul. 4, 1989

[54] SUBSTITUTED N-PHENYLPYRIDAZONE DERIVATIVES

[75] Inventors: Rainer Becker, Bad Duerkheim; Ulrich Wriede, Limburgerhof; Ulrich Schirmer, Heidelberg; Adolf Parg, Bad Duerkheim; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 54,994

[22] Filed: May 28, 1987

[30] Foreign Application Priority Data

May 28, 1986 [DE] Fed. Rep. of Germany ....... 3617997

[51] Int. Cl.$^4$ .................... A01N 43/58; C07D 237/14
[52] U.S. Cl. ........................ 71/92; 564/310; 534/558; 544/240
[58] Field of Search ............................ 544/240; 71/92

[56] References Cited

U.S. PATENT DOCUMENTS

| | | | |
|---|---|---|---|
| 4,286,092 | 8/1981 | Motta | 544/241 |
| 4,360,672 | 11/1982 | Parg et al. | 544/240 |
| 4,436,907 | 3/1984 | Holmwood et al. | 544/335 |
| 4,523,946 | 8/1985 | Parg et al. | 71/92 |
| 4,537,617 | 8/1985 | Plath et al. | 71/92 |
| 4,576,630 | 3/1986 | Parg et al. | 71/92 |
| 4,623,376 | 11/1986 | Speltz | 71/92 |
| 4,661,145 | 4/1987 | Fujimoto | 71/92 |

FOREIGN PATENT DOCUMENTS 0128530 12/1984 European Pat. Off. .

*Primary Examiner*—Mark L. Berch
*Attorney, Agent, or Firm*—Keil & Weinkauf

[57] ABSTRACT

Substituted N-phenylpyridazone derivatives of the general formula I

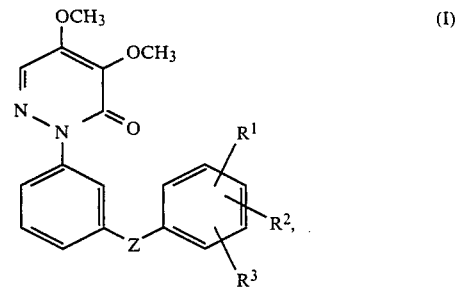

where $R^1$, $R^2$ and $R^3$ are each hydrogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-alkylsulfonyl, halogen, cyano, phenyl, phenoxy, or phenylthio and Z is a straight-chain, saturated alkylene group of 1 to 5 carbon atoms, herbicides containing these compounds, and a process for combating the growth of unwanted plants.

15 Claims, No Drawings

SUBSTITUTED N-PHENYLPYRIDAZONE DERIVATIVES

The present invention relates to novel substituted N-phenylpyridazone derivatives of the general formula (I)

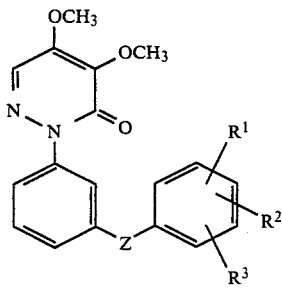

where $R^1$, $R^2$ and $R^3$ are each hydrogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-alkylsulfonyl, halogen, cyano, phenyl, phenoxy or phenylthio and Z is a straight-chain, saturated alkylene group of 1 to 5 carbon atoms.

The present invention furthermore relates to herbicides which contain the compounds I, and a method of controlling undesirable plant growth.

EP-A-128 530 discloses structurally similar compounds which differ from the compounds I in that the bridge member between the phenyl rings is interrupted by heteroatoms.

Although the known compounds have a good herbicidal action, it is an object of the present invention to provide substances which are even more effective.

We have found that this object is achieved and that the novel substituted N-phenylpyridazone derivatives I defined at the outset are very useful for controlling undesirable plant growth and are selective with respect to crops.

The compounds of type I are obtainable by the following reaction sequence:

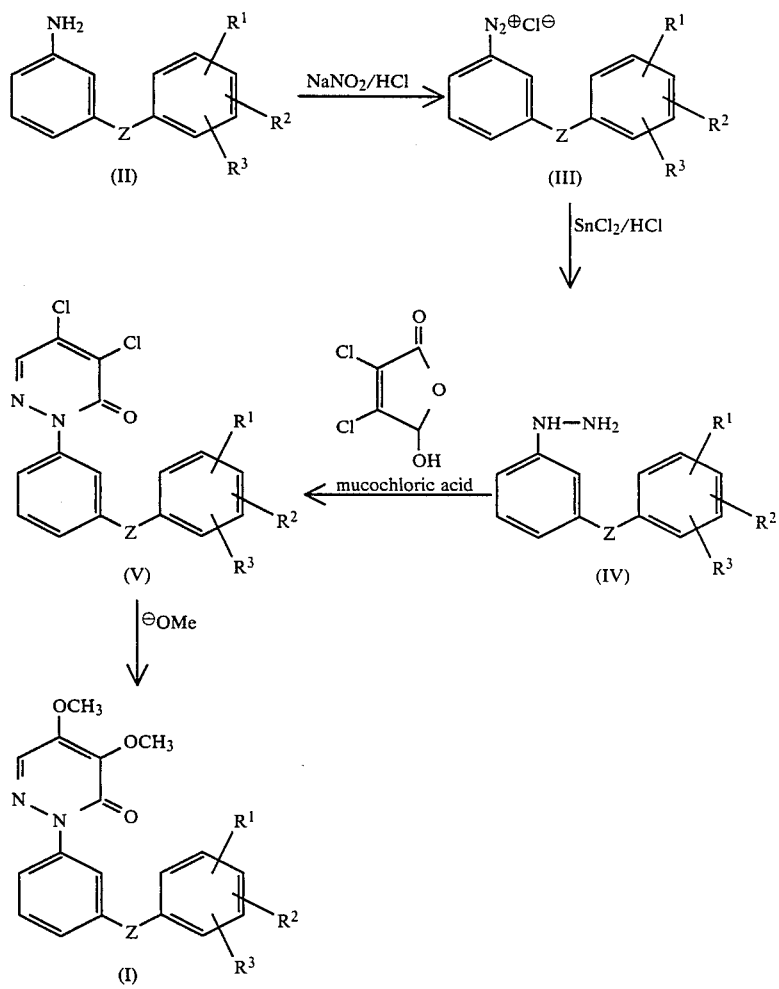

For the preparation of the compounds II

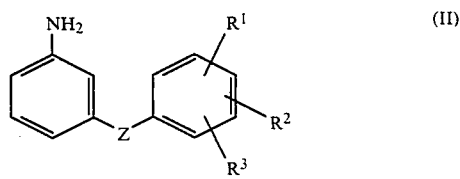

various coupling reactions are suitable for each chain length from $C_1$ to $C_5$ for Z, in particular: where Z is $CH_2$, 3-nitrobenzoyl chloride is subjected in a conventional manner to a Friedel-Crafts acylation reaction with a benzene derivative to give the 3-nitrobenzophenones

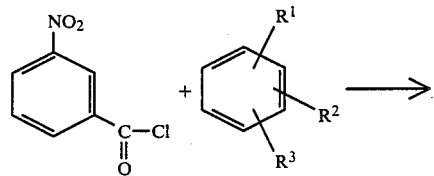

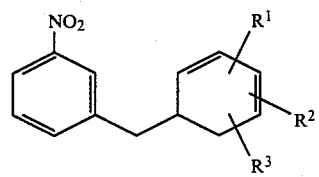

where Z is $CH_2CH_2$, 3-nitrobenzaldehyde is subjected in a conventional manner to a Wittig reaction with a benzyl-phosphonium halide to give the 3-nitrostilbenes

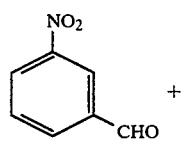

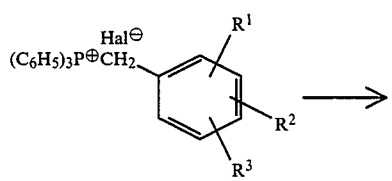

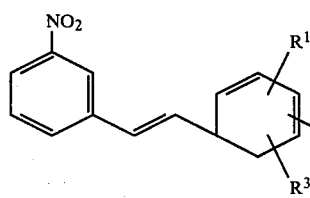

Hal = Halogen where is $CH_2CH_2CH_2$, the reaction can be carried out in a conventional manner by aldol condensation of 3-nitro-acetophenone and a benzaldehyde to give the 3-nitrobenzal-acetophenones

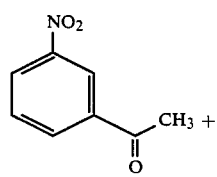

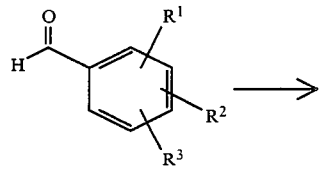

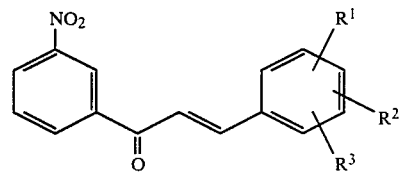

where Z is $CH_2CH_2CH_2CH_2$, 3-nitrocinnamaldehyde and a benzylphosphonium halide can be subjected to a conventional Wittig reaction to give the 1-(3-nitrophenyl)-3-phenyl-butadienes

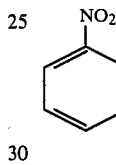

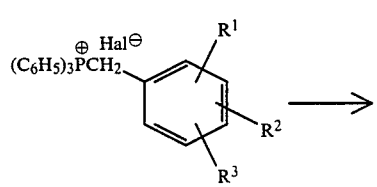

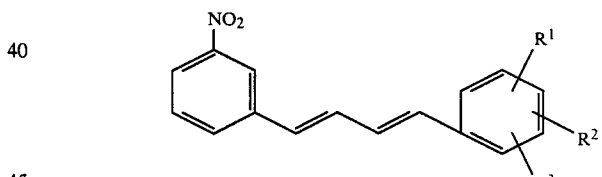

where Z is $CH_2CH_2CH_2CH_2CH_2$, 3-nitroacetophenone and a cinnamaldehyde can be subjected to an aldol condensation reaction in a conventional manner to give the 3-nitro-cinnamylideneacetophenones.

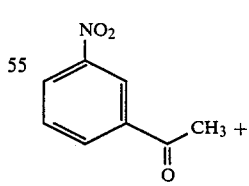

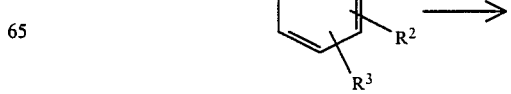

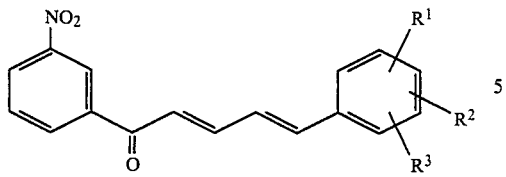

The nitro compounds and, if required, the unsaturated bridge members are hydrogenated, preferably catalytically, a conventional hydrogenation catalyst (eg. palladium on carbon, platinum sponge or Raney nickel), a suitable solvent, such as a carboxylic acid (eg. acetic acid), an ether (eg. tetrahydrofuran) or an alcohol (eg. ethanol) and, if necessary, a strong acid (eg. methane sulfonic acid or sulfuric acid) being used at from 0° to 150° C. and under from 1 to 100 bar (B. R. Baker et al., J. Pharm. Sci. 56, 737-742). The resulting anilines IV can be converted to the substituted N-phenylpyridazone derivatives I via the diazonium salt III and hydrazine derivative IV, without isolation of the intermediates.

In the case of isolation/purification of the hydrazine derivatives IV, which can be isolated, for example, as hydrochlorides, purer end products I are obtained.

The hydrazine derivatives IV can be prepared from the anilines II by a conventional method, by diazotization and reduction (Houben/Weyl, Methoden der org. Chemie, vol. 10/2, page 180 et seq, Georg-Thieme Verlag, 1967). The dihalopyridazones V can be prepared in a conventional manner (US-A-2 628 181 or EP-A-128 530) by cyclization with mucochloric acid. The novel substituted N-phenylpyridazone derivatives I can finally be obtained by reaction with a methylate, such as sodium methylate or potassium methylate, at from 0° to 150° C., preferably from 20° to 120° C., in the presence or absence of an additional solvent. Suitable solvents are hydrocarbons, eg. benzene, toluene, xylene, pentane, hexane, heptane, octane, cyclopentane or cyclohexane, ethers, eg. diethyl ether, diisopropyl ether, methyl tert-butyl ether, tetrahydrofuran, dioxane or ethylene glycol ether, and alcohols, such as methanol, ethanol, n-propanol, isopropanol, n-butanol, isobutanol or tert-butanol; benzene, toluene or xylene are preferred.

The reaction can be carried out under from 1 to 15 bar, preferably 1 bar.

$R^1$, $R^2$ and $R^3$ in the compounds I are each hydrogen or $C_1$–$C_4$-alkyl, preferably 2-, 3- or 4-methyl, 2-, 3- or 4-ethyl, 2-, 3- or 4-isopropyl, 4-tert-butyl or 2,4-, 2,5-, 2,6-, 3,4- or 3,5-dimethyl, $C_1$–$C_4$-haloalkyl, preferably 2-, 3- or 4-trifluoromethyl, $C_1$–$C_4$-alkoxy, preferably 2-, 3- or 4-methoxy, 4-tert-butoxy or 3,4-dimethoxy, $C_1$–$C_4$-haloalkoxy, preferably 2-, 3- or 4-trifluoromethoxy or 3- or 4-[(1,1,2,2)-tetrafluoroethoxy], $C_1$–$C_4$-alkylthio, preferably 3- or 4-methylthio, $C_1$–$C_4$-haloalkylthio, preferably 3- or 4-trifluoromethylthio, $C_1$–$C_4$-alkyl-sulfinyl, preferably 3- or 4-methylsulfinyl, $C_1$–$C_4$-alkyl-sulfonyl, preferably 3- or 4-methylsulfonyl, halogen, preferably 2-, 3- or 4-fluoro, 2-, 3- or 4-chloro, 3- or 4-bromo, 2,4-, 2,5-, 2,6-, 3,4- or 3,5-dichloro or 2,3,4-trichloro, cyano, preferably 4-cyano, phenyl, preferably 3- or 4-phenyl, phenoxy, preferably 3- or 4-phenoxy, or phenylthio, preferably 4-phenylthio.

Preferred compounds I include those in which one or, in particular, two of the substituents $R^1$, $R^2$ and $R^3$ are hydrogen and Z is a straight-chain, saturated alkylene group of 1 to 3 carbon atoms.

Examples of suitable compounds I are: (I)

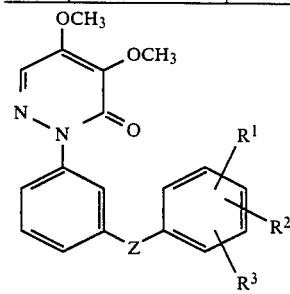

| Compound | Z | $R^1$, $R^2$, $R^3$ |
|---|---|---|
| 1 | $CH_2$ | H |
| 2 | $CH_2$ | 4-Cl |
| 3 | $CH_2$ | 4-Br |
| 4 | $CH_2$ | 4-$CH_3$ |
| 5 | $CH_2$ | 4-$OCH_3$ |
| 6 | $CH_2$ | 4-$SCH_3$ |
| 7 | $CH_2$ | 4-$SOCH_3$ |
| 8 | $CH_2$ | 4-$SO_2$—$CH_3$ |
| 9 | $CH_2$ | 2,5-dichloro |
| 10 | $CH_2$ | 3,4-dichloro |
| 11 | $CH_2$ | 2,4-dimethyl |
| 12 | $CH_2$ | 2,5-dimethyl |
| 13 | $CH_2$ | 3,4-dimethyl |
| 14 | $CH_2$ | 4-phenoxy |
| 15 | $CH_2$ | 4-phenylthio |
| 16 | $CH_2CH_2$ | H |
| 17 | $CH_2CH_2$ | 2-$CH_3$ |
| 18 | $CH_2CH_2$ | 3-$CH_3$ |
| 19 | $CH_2CH_2$ | 4-$CH_3$ |
| 20 | $CH_2CH_2$ | 4-i-$C_3H_7$ |
| 21 | $CH_2CH_2$ | 4-t-$C_4H_9$ |
| 22 | $CH_2CH_2$ | 4-phenyl |
| 23 | $CH_2CH_2$ | 2,4-dimethyl |
| 24 | $CH_2CH_2$ | 2,5-dimethyl |
| 25 | $CH_2CH_2$ | 3,4-dimethyl |
| 26 | $CH_2CH_2$ | 2-$CF_3$ |
| 27 | $CH_2CH_2$ | 3-$CF_3$ |
| 28 | $CH_2CH_2$ | 4-$CF_3$ |
| 29 | $CH_2CH_2$ | 2-F |
| 30 | $CH_2CH_2$ | 3-F |
| 31 | $CH_2CH_2$ | 4-F |
| 32 | $CH_2CH_2$ | 2-Cl |
| 33 | $CH_2CH_2$ | 3-Cl |
| 34 | $CH_2CH_2$ | 4-Cl |
| 35 | $CH_2CH_2$ | 4-Br |
| 36 | $CH_2CH_2$ | 2,6-dichloro |
| 37 | $CH_2CH_2$ | 2,4-dichloro |
| 38 | $CH_2CH_2$ | 3,4-dichloro |
| 39 | $CH_2CH_2$ | 3,5-dichloro |
| 40 | $CH_2CH_2$ | 2,5-dichloro |
| 41 | $CH_2CH_2$ | 2,3,4-trichloro |
| 42 | $CH_2CH_2$ | 4-CN |
| 43 | $CH_2CH_2$ | 2-$OCH_3$ |
| 44 | $CH_2CH_2$ | 3-$OCH_3$ |
| 45 | $CH_2CH_2$ | 4-$OCH_3$ |
| 46 | $CH_2CH_2$ | 4-O—t-$C_4H_9$ |
| 47 | $CH_2CH_2$ | 3-phenoxy |
| 48 | $CH_2CH_2$ | 4-phenoxy |
| 49 | $CH_2CH_2$ | 3,4-dimethoxy |
| 50 | $CH_2CH_2$ | 4-$SCH_3$ |
| 51 | $CH_2CH_2$ | 3-$OCF_2CHF_2$ |
| 52 | $CH_2CH_2$ | 4-$OCF_2CHF_2$ |
| 53 | $CH_2CH_2CH_2$ | H |
| 54 | $CH_2CH_2CH_2$ | 2-$CH_3$ |
| 55 | $CH_2CH_2CH_2$ | 3-$CH_3$ |
| 56 | $CH_2CH_2CH_2$ | 4-$CH_3$ |
| 57 | $CH_2CH_2CH_2$ | 4-i-$C_3H_7$ |
| 58 | $CH_2CH_2CH_2$ | 4-t-$C_4H_9$ |
| 59 | $CH_2CH_2CH_2$ | 4-phenyl |
| 60 | $CH_2CH_2CH_2$ | 2,4-dimethyl |
| 61 | $CH_2CH_2CH_2$ | 3,4-dimethyl |
| 62 | $CH_2CH_2CH_2$ | 3,5-dimethyl |
| 63 | $CH_2CH_2CH_2$ | 2-F |
| 64 | $CH_2CH_2CH_2$ | 3-F |
| 65 | $CH_2CH_2CH_2$ | 4-F |

-continued

Examples of suitable compounds I are:

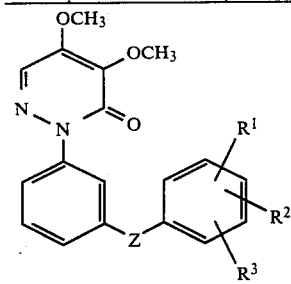

(I)

| Compound | Z | R¹, R², R³ |
|---|---|---|
| 66 | $CH_2CH_2CH_2$ | 2-Cl |
| 67 | $CH_2CH_2CH_2$ | 3-Cl |
| 68 | $CH_2CH_2CH_2$ | 4-Cl |
| 69 | $CH_2CH_2CH_2$ | 2,6-dichloro |
| 70 | $CH_2CH_2CH_2$ | 2,5-dichloro |
| 71 | $CH_2CH_2CH_2$ | 3,4-dichloro |
| 72 | $CH_2CH_2CH_2$ | 3,5-dichloro |
| 73 | $CH_2CH_2CH_2$ | 2,4-dichloro |
| 74 | $CH_2CH_2CH_2$ | 4-Br |
| 75 | $CH_2CH_2CH_2$ | 2-$CF_3$ |
| 76 | $CH_2CH_2CH_2$ | 3-$CF_3$ |
| 77 | $CH_2CH_2CH_2$ | 4-$CF_3$ |
| 78 | $CH_2CH_2CH_2$ | 2-$OCH_3$ |
| 79 | $CH_2CH_2CH_2$ | 3-$OCH_3$ |
| 80 | $CH_2CH_2CH_2$ | 4-$OCH_3$ |
| 81 | $CH_2CH_2CH_2$ | 3,4-dimethoxy |
| 82 | $CH_2CH_2CH_2$ | 4-O—t-$C_4H_9$ |
| 83 | $CH_2CH_2CH_2$ | 3-phenoxy |
| 84 | $CH_2CH_2CH_2$ | 4-phenoxy |
| 85 | $CH_2CH_2CH_2$ | 4-$SCH_3$ |
| 86 | $CH_2CH_2CH_2$ | 3-$OCF_2CHF_2$ |
| 87 | $CH_2CH_2CH_2$ | 4-$OCF_2CHF_2$ |
| 88 | $CH_2CH_2CH_2$ | 4-CN |
| 89 | $CH_2CH_2CH_2CH_2$ | H |
| 90 | $CH_2CH_2CH_2CH_2$ | 3-$CH_3$ |
| 91 | $CH_2CH_2CH_2CH_2$ | 4-$CH_3$ |
| 92 | $CH_2CH_2CH_2CH_2$ | 4-t-$C_4H_9$ |
| 93 | $CH_2CH_2CH_2CH_2$ | 2,4-dimethyl |
| 94 | $CH_2CH_2CH_2CH_2$ | 3-F |
| 95 | $CH_2CH_2CH_2CH_2$ | 4-F |
| 96 | $CH_2CH_2CH_2CH_2$ | 2-Cl |
| 97 | $CH_2CH_2CH_2CH_2$ | 3-Cl |
| 98 | $CH_2CH_2CH_2CH_2$ | 4-Cl |
| 99 | $CH_2CH_2CH_2CH_2$ | 2,4-dichloro |
| 100 | $CH_2CH_2CH_2CH_2$ | 3,5-dichloro |
| 101 | $CH_2CH_2CH_2CH_2$ | 3,4-dichloro |
| 102 | $CH_2CH_2CH_2CH_2$ | 3-$CF_3$ |
| 103 | $CH_2CH_2CH_2CH_2$ | 4-$CF_3$ |
| 104 | $CH_2CH_2CH_2CH_2$ | 3-$OCH_3$ |
| 105 | $CH_2CH_2CH_2CH_2$ | 4-$OCH_3$ |
| 106 | $CH_2CH_2CH_2CH_2$ | 4-$SCH_3$ |
| 107 | $(CH_2)_5$ | H |
| 108 | $(CH_2)_5$ | 4-Cl |
| 109 | $CH_2$ | 4-F |
| 110 | $CH_2CH_2CH_2$ | 2,3,4-trichloro |
| 111 | $(CH_2)_5$ | 4-F |

The substituted N-phenylpyridazone derivatives I, or herbicidal agents containing them may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are suitable for the preparation of directly sprayable solutions, emulsions, pastes and oil dispersions from mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methyl-pyrrolidone, water, etc.

Aqueous formulations may be prepared from emulsion concentrates, pastes, dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salt of aromatic sulfonic acids, e.g., ligninsulfonic acid, naphthalenesulfonic acid, dibutylnaphthalenesulfonic acid, and phenolsulfonic acid, and of fatty acids, alkyl and alkylaryl sulfonates, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetate, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 19 is mixed with 10 parts by weight of N-methyl-alpha-pyrrolidone. A mixture is obtained which is suitable for application in the form of very fine drops.

II. 20 parts by weight of compound no. 53 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 30 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 29 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 37 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3 is intimately mixed with 97 parts by weight of particulate kaolin. A dust is obtained containing 3% by weight of the active ingredient.

VII. 30 parts by weight of compound no. 33 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 44 is intimately mixed with 2 parts by weight of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 40 parts by weight of compound no. 65 is dissolved in 60 parts by weight of a mixture cnsisting of 93 wt% of xylene and 7 wt% of the adduct of 8 moles of ethylene oxide and 1 mole of nonyl phenol. A solution is obtained containing 40 wt% of the active ingredient.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of year, the plants to be combated and their growth stage, and varies from 0.01 to 5.0, preferably from 0.05 to 0.5, kg/ha.

In view of the spectrum of weeds that can be combated, the tolerance of the active ingredients by crop plants, and in view of the numerous application methods availale, the active ingredients according to the invention may, depending on the substitution pattern, be used in a large number of crops. The following may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | bermudagrass |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactua sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |

-continued

| Botanical name | Common name |
| --- | --- |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn sweet corn, maize |

To increase the spectrum of action and to achieve synergistic effects, the substituted N-phenylpyridazone derivatives of the general formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

MANUFACTURING EXAMPLES

Manufacture of compounds I

At 0° to 7° C., a solution of 13.5 g of sodium nitrite in 30 ml of water was added dropwise to a solution of 192 mmol of an aniline II in 290 ml of glacial acetic acid and 68 ml of concentrated hydrochloric acid. After the mixture had been stirred for 1 hour at 5° C., a solution of 58 g of tin(II) chloride dihydrate in 77 ml of concentrated hydrochloric acid was dripped in in such a manner that the temperature did not exceed 5° C. Subsequent heating to 20° C., stirring for 30 minutes and addition of 32 g of mucochloric acid over a 5-minute period followed by refluxing for 5 minutes gave a reaction mixture which was poured into ice water. Extraction was then carried out with methylene chloride. The organic phase was washed with water, dried and concentrated. The crude product was purified by chromatography on silica gel using methylene chloride/pentane as the mobile phase.

110 g of sodium methylate was added to 65 mmol of a dichloropyridazone V in 300 ml of toluene. The mixture was stirred for 2 to 4 hours at 60° to 75° C. 400 ml of methylene chloride was added and the solution was washed three times with water, dried and concentrated. The crude product was purified by chromatography on silica gel using methyl tert-butyl ether/pentane as the mobile phase.

The results obtained are given in the following table.

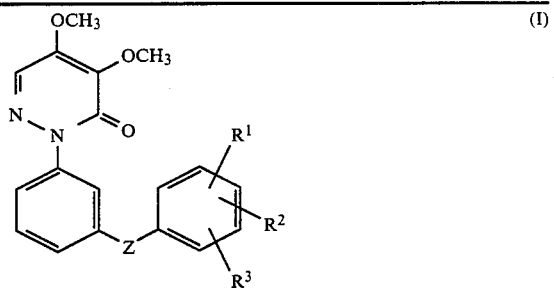

(I)

| Comp. no. | Z | $R^1, R^2, R^3$ | M.p. [°C.] | IR [cm$^{-1}$] | $^1$H—NMR [ppm] |
| --- | --- | --- | --- | --- | --- |
| 1 | $CH_2$ | H | 105–106 | | |
| 2 | $CH_2$ | 4-Cl | 72–73 | | |
| 3 | $CH_2$ | 4-Br | | | 8.20 (s, 1H) |
| 4 | $CH_2$ | 4-$CH_3$ | 52–53 | | |
| 5 | $CH_2$ | 4-$OCH_3$ | | 1652 (C=O) | |
| 6 | $CH_2$ | 4-$SCH_3$ | | | 8.19 (s, 1H) |
| 13 | $CH_2$ | 3,4-dimethyl | | 1653 (C=O) | |
| 16 | $CH_2CH_2$ | H | 78–81 | | |
| 17 | $CH_2CH_2$ | 2-$CH_3$ | 85–87 | | |
| 18 | $CH_2CH_2$ | 3-$CH_3$ | 68–70 | | |
| 19 | $CH_2CH_2$ | 4-$CH_3$ | 100–102 | | |
| 21 | $CH_2CH_2$ | 4-t-$C_4H_9$ | | | 7.83 (s, 1H) |
| 27 | $CH_2CH_2$ | 3-$CF_3$ | 89–90 | | |
| 28 | $CH_2CH_2$ | 4-$CF_3$ | 96–97 | | |
| 29 | $CH_2CH_2$ | 2-F | 116–118 | | |
| 30 | $CH_2CH_2$ | 3-F | 60–61 | | |
| 31 | $CH_2CH_2$ | 4-F | 78–80 | | |
| 33 | $CH_2CH_2$ | 3-Cl | 58–60 | | |
| 34 | $CH_2CH_2$ | 4-Cl | 87–88 | | |
| 36 | $CH_2CH_2$ | 2,6-dichloro | 89–91 | | |
| 37 | $CH_2CH_2$ | 2,4-dichloro | 80–82 | | |
| 38 | $CH_2CH_2$ | 3,4-dichloro | 74–76 | | |
| 40 | $CH_2CH_2$ | 2,5-dichloro | 102–103 | | |
| 44 | $CH_2CH_2$ | 3-$OCH_3$ | | 1652 (C=O) | |
| 45 | $CH_2CH_2$ | 4-$OCH_3$ | 68–70 | | |

-continued

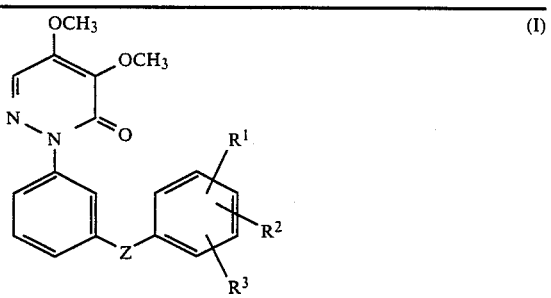

| Comp. no. | Z | $R^1, R^2, R^3$ | M.p. [°C.] | IR [cm$^{-1}$] | $^1$H—NMR [ppm] |
|---|---|---|---|---|---|
| 50 | CH$_2$CH$_2$ | 4-SCH$_3$ | 68–69 | | |
| 53 | CH$_2$CH$_2$CH$_2$ | H | 73–75 | | |
| 54 | CH$_2$CH$_2$CH$_2$ | 2-CH$_3$ | 38–40 | | |
| 55 | CH$_2$CH$_2$CH$_2$ | 3-CH$_3$ | 47–49 | | |
| 56 | CH$_2$CH$_2$CH$_2$ | 4-CH$_3$ | 68–70 | | |
| 57 | CH$_2$CH$_2$CH$_2$ | 4-i-C$_3$H$_7$ | 55–56 | | |
| 58 | CH$_2$CH$_2$CH$_2$ | 4-t-C$_4$H$_9$ | | 1654 (C=O) | |
| 59 | CH$_2$CH$_2$CH$_2$ | 4-phenyl | | 1652 (C=O) | |
| 60 | CH$_2$CH$_2$CH$_2$ | 2,4-dimethyl | 50–50,5 | | |
| 63 | CH$_2$CH$_2$CH$_2$ | 2-F | 60–61 | | |
| 64 | CH$_2$CH$_2$CH$_2$ | 3-F | | 1653 (C=O) | |
| 65 | CH$_2$CH$_2$CH$_2$ | 4-F | 61–63 | | |
| 67 | CH$_2$CH$_2$CH$_2$ | 3-Cl | 53–55 | | |
| 68 | CH$_2$CH$_2$CH$_2$ | 4-Cl | | | 7.83 (s, 1H) |
| 69 | CH$_2$CH$_2$CH$_2$ | 2,6-dichloro | 107–109 | | |
| 70 | CH$_2$CH$_2$CH$_2$ | 2,5-dichloro | 86–88 | | |
| 71 | CH$_2$CH$_2$CH$_2$ | 3,4-dichloro | | 1651 (C=O) | |
| 72 | CH$_2$CH$_2$CH$_2$ | 3,5-dichloro | | 1652 (C=O) | |
| 73 | CH$_2$CH$_2$CH$_2$ | 2,4-dichloro | 118–119 | | |
| 76 | CH$_2$CH$_2$CH$_2$ | 3-CF$_3$ | 81–83 | | |
| 77 | CH$_2$CH$_2$CH$_2$ | 4-CF$_3$ | | 1633 (C=O) | |
| 79 | CH$_2$CH$_2$CH$_2$ | 3-OCH$_3$ | 96–98 | | |
| 80 | CH$_2$CH$_2$CH$_2$ | 4-OCH$_3$ | | 1652 (C=O) | |
| 81 | CH$_2$CH$_2$CH$_2$ | 3,4-dimethoxy | | 1653 (C=O) | |
| 83 | CH$_2$CH$_2$CH$_2$ | 3-phenoxy | | | 7.82 (s, 1H) |
| 86 | CH$_2$CH$_2$CH$_2$ | 3-OCF$_2$CHF$_2$ | 40–45 | | |
| 87 | CH$_2$CH$_2$CH$_2$ | 4-OCF$_2$CHF$_2$ | | 1652 (C=O) | |
| 89 | CH$_2$CH$_2$CH$_2$CH$_2$ | H | | 1653 (C=O) | |
| 107 | (CH$_2$)$_5$ | H | | 1652 (C=O) | |
| 109 | CH$_2$ | 4-F | 108–110 | | |
| 110 | CH$_2$CH$_2$CH$_2$ | 2,3,4-trichloro | 83–85 | | |
| 111 | (CH$_2$)$_5$ | 4-F | | | 8.23 (s, 1H) |

USE EXAMPLES

The herbicidal action of the N-phenylpyridazones of the formula I when applied postemergence to test plants is demonstrated in the following greenhouse experiments.

The vessels employed were plastic flowerpots having a volume of 300 cm$^3$ and which were filled with a sandy loam containing about 3.0% humus. Peat was added to the soybean plants to improve the stand. The seeds of the test plants were sown shallow, and separately, according to species.

For the postemergence treatment, plants were selected which had been sown directly in the vessels and had grown there, or which had been grown separately as seedlings and transplanted to the vessels a few days before treatment.

The plants were first grown to a height of from 3 to 15 cm, depending on growth form, before being treated. The active ingredients were suspended or emulsified in water as vehicle and sprayed through finely distributing nozzles. The application rates on postemergence treatment varied from 0.06 to 0.25 kg of active ingredient per hectare.

The vessels were set up in the greenhouse—species from warmer areas at from 20° to 35° C., and species from moderate climates at from 10° to 20° C. The experiments were run for from 2 to 4 weeks. During this period the plants were tended and their reactions to the various treatments assessed.

The following plants were investigated as to their reaction to compounds I and prior art compounds: *Abutilon theophrasti, Amaranthus retroflexus, Arachis hypogaea, Cassia tora, Centaurea cyanus, Chenopodium album, Chrysanthemum coronarium, Desmodium tortuosum, Euphorbia heterophylla, Galium aparine, Glycine max., Ipomoea spp., Lamium amplexicaule, Mercurialis annua, Polygonum persicaria, Stellaria media, Solanum nigrum, Triticum aestivum,* and *Zea mays.*

As comparative substances I', active ingredients were employed which are known from EP-A-128,530 and in which Z' is an oxygen- or sulfur-containing chain; they are compared with the novel active ingredients having the same chain length for Z.

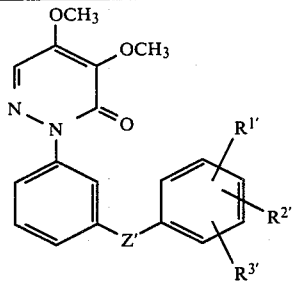

| Comp. substances I' | Z' | R1', R2', R3' | Ex. in EP-A-128 530 |
|---|---|---|---|
| A | CH2S | 4-CH3 | 114 |
| B | CH2O | 4-CH3 | 24 |
| C | CH2O | H | 1 |
| D | SCH2 | H | 126 |
| E | CH2S | H | 105 |
| F | CH2OCH2 | H | 102 |
| G | OCH2CH2 | H | 87 |
| H | CH2O | 3-F | 3 |
| I | OCH2 | 3-F | 64 |
| K | CH2O | 2,4-dichloro | 13 |
| L | OCH2 | 3-chloro | 67 |
| M | CH2O | 4-SCH3 | 46 |

At an application rate of 0.06 kg/ha, compound 19 combated unwanted dicotyledonous plants much better than comparative substance A, and was well tolerated by groundnuts.

For the selective control of dicotyledonous plants, compound 19, at a rate of 0.06 kg/ha, proved to be more suitable than prior art compounds A and B. There was hardly any difference between the compounds as regards tolerance by wheat.

Compound 16, applied at a rate of 0.06 kg/ha, combated a broad spectrum of unwanted dicotyledonous plants. Indian corn, as an example of a monocotyledonous crop plant, suffered no appreciable damage. Comparative substances C, D and E had a significantly weaker herbicidal action and also caused considerable damage to the crop plant.

Compound 53, at a rate of 0.125 kg/ha, gave good control of injurious dicotyledonous plants; groundnut plants were not affected. The level of herbicidal action of comparative substance F was much lower.

Compound 53 was employed at a rate of 0.125 kg/ha for combating unwanted dicotyledonous plants. No appreciable damage was caused to wheat. Comparative substances F and G, applied at the same rate, exhibited much weaker herbicidal properties.

A broad spectrum of unwanted plants was well controlled by 0.06 kg/ha of compound 30. The level of herbicidal action of comparative substances H and I was much lower. Wheat suffered no damage when compounds 30, H and I were applied. Compounds 30 and H caused slight damage to Indian corn, and compound I heavier damage.

Compound 37, at 0.125 kg/ha, gave better control of unwanted plants than comparative substance K; no appreciable damage was caused to groundnut plants by either compound.

A broad spectrum of unwanted plants was combated by compound 33 (at a rate of 0.06 kg/ha) much better than comparative substance L.

At a rate of 0.05 kg/ha, compound 50 combated unwanted broadleaved plants well without damaging soybeans. Comparative substance M, at the same rate, had a much weaker herbicidal action and caused slight damage to soybeans.

We claim:

1. A substituted N-phenylpyridazone of the formula I

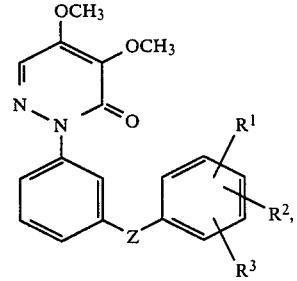

where $R^1$ is hydrogen and $R^2$ and $R^3$ are the same or different and each is hydrogen, $C_1-C_4$-alkyl, $C_1-C_4$-haloalkyl, $C_1-C_4$-alkoxy, $C_1-C_4$-alkylthio, $C_1-C_4$-haloalkylthio, $C_1-C_4$-alkylsulfinyl, $C_1-C_4$-alkylsulfonyl, halogen, cyano, phenyl, phenoxy, or phenylthio and Z is a straight-chain, saturated alkylene group of 2 to 5 carbon atoms.

2. A substituted N-phenylpyridazone of the formula I as set forth in claim 1, where $R^1$ is hydrogen and $R^2$ and $R^3$ are the same or different and each is hydrogen, $C_1-C_4$-alkyl, $C_1-C_4$-haloalkyl, $C_1-C_4$-alkoxy, $C_1-C_4$-alkylthio, halogen or phenyl, and Z is a straight-chain, saturated alkylene group of 2 to 3 carbon atoms.

3. A substituted N-phenylpyridazone of the formula I as set forth in claim 1, where $R^1$ is hydrogen and $R^2$ and $R^3$ are the same or different and each is hydrogen, $C_1-C_4$-alkyl, $C_1-C_4$-haloalkyl, $C_1-C_4$-alkoxy, $C_1-C_4$-alkylthio, halogen or phenyl, and Z is a straight-chain, saturated alkylene group of 2 to 3 carbon atoms.

4. A substituted N-phenylpyridazone of the formula I as set forth in claim 1, where $R^1$ and $R^2$ are each hydrogen, $R^3$ is hydrogen, $C_1-C_4$-alkyl, $C_1-C_4$-haloalkyl, $C_1-C_4$-alkoxy, $C_1-C_4$-alkylthio, halogen or phenyl, and Z is a straight-chain, saturated alkylene group of 2 to 3 carbon atoms.

5. A substituted N-phenylpyridazone of the formula I as set forth in claim 1, where $R^1$ and $R^2$ are each hydrogen, $R^3$ is 4-fluoro and Z is $-CH_2-CH_2-$.

6. A substituted N-phenylpyridazone of the formula I as set forth in claim 1, wherein $R^1$ is hydrogen, $R^2$ is hydrogen and $R^3$ is 4—$SCH_3$.

7. A herbicide containing inert additives and a substituted N-phenylpyridazone of the formula I as set forth in claim 1.

8. A process for combating the growth of unwanted plants, wherein the unwanted plants are treated with a herbicidally effective amount of a substituted N-phenylpyridazone of the formula I as set forth in claim 1.

9. A substituted N-phenylpyridazone of the formula I as set forth in claim 1, where $R^1$ and $R^2$ are each hydrogen, $R^3$ is 4—$CH_3$ and Z is $-CH_2-CH_2-$.

10. A substituted N-phenylpyridazone of the formula I as set forth in claim 1, where $R^1$, $R^2$ and $R^3$ are each hydrogen and Z is $-CH_2-CH_2-$.

11. A substituted N-phenylpyridazone of the formula I as set forth in claim 1, where $R^1$ and $R^2$ are each hydrogen, $R^3$ is 3—F, and Z is $-CH_2-CH_2-$.

12. A substituted N-phenylpyridazone of the formula I as set forth in claim 1, where $R^1$ and $R^2$ are each hydrogen, where $R^3$ is 3—Cl and Z is —$CH_2$—$CH_2$—.

13. A substituted N-phenylpyridazone of the formula I as set forth in claim 1, where $R^1$ is hydrogen, $R^2$ is Cl, $R^3$ is 6—Cl and Z is —$CH_2$—$CH_2$—.

14. A substituted N-phenylpyridazone of the formula I as set forth in claim 1, where $R^1$, $R^2$ and $R^3$ are each hydrogen and Z is —$(CH_2)_3$—.

15. A substituted N-phenylpyridazone of the formula I as set forth in claim 1, wherein $R^1$ is hydrogen, $R^2$ is 2—Cl and $R^3$ is 4—Cl.

* * * * *